US009687432B2

(12) United States Patent
Gruber et al.

(10) Patent No.: US 9,687,432 B2
(45) Date of Patent: Jun. 27, 2017

(54) ANTIMICROBIAL BISPYRIDINE AMINE COMPOSITIONS AND USES

(71) Applicant: LONZA INC., Allendale, NJ (US)

(72) Inventors: James V. Gruber, Washington, NJ (US); Diana Ciccognani, Bury (GB); Volodymyr B. Pashovych, Alpharetta, GA (US)

(73) Assignee: LONZA INC., Allendale, NJ (US)

( * ) Notice: Subject to any disclaimer, the term of this patent is extended or adjusted under 35 U.S.C. 154(b) by 70 days.

(21) Appl. No.: 14/654,025

(22) PCT Filed: Dec. 23, 2013

(86) PCT No.: PCT/US2013/077428
§ 371 (c)(1),
(2) Date: Jun. 19, 2015

(87) PCT Pub. No.: WO2014/100807
PCT Pub. Date: Jun. 26, 2014

(65) Prior Publication Data

US 2015/0328115 A1 Nov. 19, 2015

Related U.S. Application Data

(60) Provisional application No. 61/740,512, filed on Dec. 21, 2012, provisional application No. 61/752,707, filed on Jan. 15, 2013.

(51) Int. Cl.
*A61K 8/49* (2006.01)
*A61K 31/4425* (2006.01)
(Continued)

(52) U.S. Cl.
CPC ............ *A61K 8/4926* (2013.01); *A61K 8/361* (2013.01); *A61K 31/4425* (2013.01);
(Continued)

(58) Field of Classification Search
None
See application file for complete search history.

(56) References Cited

U.S. PATENT DOCUMENTS 4,206,215 A 6/1980 Bailey
5,370,875 A 12/1994 Rogozinski
(Continued)

FOREIGN PATENT DOCUMENTS

EP 1683416 A1 7/2006
WO 2009106468 A2 9/2009
WO 2012031984 A2 3/2012

OTHER PUBLICATIONS

Supplementary European Search Report, dated Apr. 29, 2016, issued in corresponding International Application EP 13 86 6270.

*Primary Examiner* — Robert A Wax
*Assistant Examiner* — Melissa Mercier
(74) *Attorney, Agent, or Firm* — Gianna J. Arnold; Saul Ewing LLP

(57) ABSTRACT

Antimicrobial bispyridine amine compositions that facilitate easy application on the skin, do not penetrate the skin, are compatible with typical deodorant ingredients, and do not cause adverse effects on skin and clothing. In one aspect, the present invention relates to an antimicrobial composition including an organic acid salt of a bispyridine amine where the organic acid contains from about 4 to about 30 carbon atoms. Because the organic acid salts of bispyridine amines are large molecules, they will not easily penetrate the skin, and will stay on the surface where they were applied and where they are needed to have their effect.

17 Claims, 2 Drawing Sheets

(51) Int. Cl.
*A61Q 15/00* (2006.01)
*A61Q 17/00* (2006.01)
*A61K 8/36* (2006.01)
*C11D 3/48* (2006.01)

(52) U.S. Cl.
CPC ........... *A61Q 15/00* (2013.01); *A61Q 17/005* (2013.01); *C11D 3/48* (2013.01)

(56) References Cited

U.S. PATENT DOCUMENTS

2004/0092588 A1 5/2004 Kramer et al.
2006/0165612 A1 7/2006 Beilfuss et al.
2007/0255004 A1 11/2007 Lohrmann et al.
2009/0297458 A1* 12/2009 Ruppert ............... A61K 6/0017 424/49
2011/0003857 A1 1/2011 Beilfuss et al.
2011/0091551 A1 4/2011 Baur et al.

* cited by examiner

ANTIMICROBIAL BISPYRIDINE AMINE COMPOSITIONS AND USES

CROSS REFERENCE TO RELATED APPLICATIONS

This application claims the priority of PCT/US2013/077428, filed on 23 Dec. 2013, which claims priority to U.S. Application Nos. 61/740,512 filed 21 Dec. 2012, and U.S. 61/752,707, filed 15 Jan. 2013, the entire contents of each of which are hereby incorporated in total by reference.

FIELD OF THE INVENTION

The invention relates generally to an antimicrobial composition comprising a bispyridine amine. The antimicrobial composition comprising a bispyridine amine is advantageously used in personal care and cosmetic preparations such as, for example, a deodorant, hair cleansing preparation, a preparation for the treatment of blemished, oily skin, comedones, and foot odor. The antimicrobial composition comprising bispyridine amine is also advantageously used as a bacteriostatic/bactericidal agent for use in wound cleaning and as a disinfectant in treating hard surfaces. In a at least one embodiment, the bispyridine amine used according to the invention is an octenidine distearate.

BACKGROUND OF THE INVENTION

Secretions from the apocrine sweat glands, which are primarily located in the human underarm, are largely odorless. The human underarm is consistently warm, and sweat glands present in the underarm provide moisture, which when excreted, has a vital cooling effect. When adult underarms are washed with alkaline pH soap, the skin loses its acid mantle (pH 4.5-6), raising the skin pH and disrupting the skin barrier. Many bacteria thrive at this elevated pH, making the skin susceptible to bacterial colonization. The bacteria feed on the secretions from the apocrine glands, and on dead skin and hair cells, which results in the degradation of long-chain fatty acids into shorter chain acids such as formic acid or butyric acid, which are the primary cause of body odor.

Deodorants function in many ways to eliminate odor. For example, they are able to mask or complement the odor to minimize the offensive smell; trap the odor so that the volatile components do not reach the nose; or prevent or slow down the generation of volatile odiferous chemicals. Deodorants can also be formulated with antimicrobials to slow bacterial growth. For such formulations to be effective, antimicrobials should be easily applied and remain active on the skin for many hours. Inhibitors of perspiration (antiperspirants), which directly influence the secretion of perspiration, are also used to eliminate body odor. For easy application, antimicrobials need to be compatible with typical deodorant ingredients and, for consumer acceptance should not have adverse effects on skin. Additionally, deodorants should be developed so as to not react with sweat or create yellow stains on clothing.

Octenidine, in particular octenidine dihydrochloride, is an antimicrobial agent which has been previously described for use in antiseptic agents for the skin, the mucous membranes and wound antisepsis. Octenidine is known to strongly adhere to lipid components in cell membranes, which contributes to its high antimicrobial effect while at the same time being well tolerated by the human epithelia and traumatic tissues. Octenidine primarily acts anti-bacterially due to its affinity to bacterial surfaces. Consequently, the inclusion of octenidine, in particular octenidine dihydrochloride, in antiseptic preparations has been effective against microorganisms which contribute to, for example, body odor, blemished and/or oily skin, comedones, dandruff and foot odor.

Additionally, octenidine dihydrochloride has a disinfecting/antimicrobial effect against fungi and viruses. Consequently, the inclusion of octenidine hydrochloride in preparations for use in wound cleaning and as a disinfectant in treating hard surfaces such as, for example, operating room tables and laboratory equipment has also been previously described.

Octenidine and octenidine dihydrochloride are described in U.S. Pat. Nos. 4,206,215 and 4,442,124 as antimicrobial preparations and in U.S. Publication No. US2011/0217360 for wound and mucous membrane antisepsis, each of which is hereby incorporated by reference.

Although the benefits of octenidine are well documented, it has recently emerged that, as described in U.S. Publication No. US2011/0003857, antimicrobial octenidine compositions, such as octenidine dihydrochloride, have a tendency towards decomposition upon prolonged storage, for example, a period of several months. It is also established that degradation products can form from octenidine dihydrochloride alone and when used in combination with certain auxiliaries, which causes peroxides and aldehydes to form. Moreover, when antimicrobial octenidine dihydrochloride compositions are used in aerosol containers made of, for example, tinplate, aluminum, stainless steel, and other metals, the octenidine composition has caused corrosion in the aerosol container.

Thus, there is a need for antimicrobial compositions that facilitate easy application on the skin, do not penetrate the skin, are compatible with typical deodorant and cosmetic ingredients, and do not cause adverse effects (e.g., irritation) to skin and clothing. Additionally, there is also a need for antimicrobial compositions for use in wound cleaning and as a biocide for treating hard surfaces. Moreover, there is a need for antimicrobial compositions that are stable when stored at a comparatively high concentration, even at elevated temperatures, without degradation, formation of decomposition products or reduction in active ingredient content and do not cause corrosion of the dispenser.

SUMMARY OF THE INVENTION

The present invention, therefore, is directed to antimicrobial bispyridine amine compositions that facilitate easy application on the skin, do not penetrate the skin, are compatible with typical deodorant ingredients, and do not cause adverse effects on skin and clothing. In one aspect, the present invention relates to an antimicrobial composition including an organic acid salt of a bispyridine amine where the organic acid contains from about 4 to about 30 carbon atoms. Because the organic acid salts of bispyridine amines are large molecules, they will not easily penetrate the skin, and will stay on the surface where they were applied and where they are needed to have their effect.

In one embodiment, the bispyridine amine is an octenidine distearate. In a one embodiment, the bispyridine amine is added to, and is compatible with, ingredients typically used in personal care and cosmetics. In an alternative embodiment, the bispyridine amine is added to, and is compatible with, ingredients typically used for wound cleansing and as a biocide. These and other aspects will become apparent upon reading the following detailed description of the present invention.

DETAILED DESCRIPTION OF THE INVENTION

Figure 1:
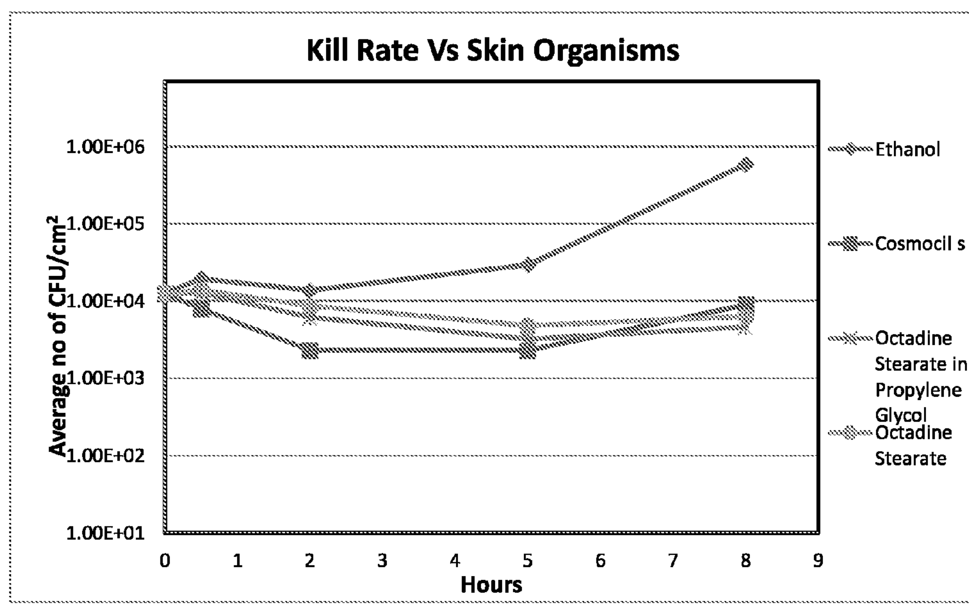
FIG. 1 depicts the average number of bacterial colony forming units per square centimeter (CFU/$cm^2$) of skin over an 8 hour time period after application of ethanol, Cosmocil® S, octenidine distearate and octenidine distearate in propylene glycol.

The present invention, therefore, is directed to antimicrobial bispyridine amine compositions that do not irritate the skin, facilitate easy application on the skin, do not penetrate the skin, stay on the surface of the skin where applied, do not cause adverse effects on the skin and clothing, and are compatible with ingredients typically used in personal care and cosmetic preparations such as, for example, a deodorant, hair cleansing preparation, a preparation for the treatment of blemished, oily skin, comedones, and foot odor. In one aspect, the present invention is directed to an antimicrobial bispyridine amine composition having the general formula:

(I)

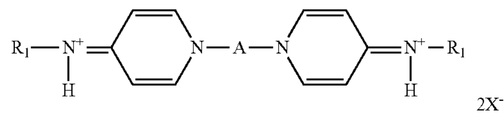

or acceptable salts thereof, wherein $R^1$ is selected from a group consisting of hydrogen, $C_1$-$C_{20}$ linear or branched hydrocarbon, which may be saturated or unsaturated and may be optionally substituted with a halogen, or a hydroxyl group. Examples of $C_1$-$C_{20}$ hydrocarbons include $C_1$-$C_{20}$ linear alkyl, $C_4$-$C_{20}$ branched alkyl, $C_6$-$C_{20}$ cyclic alkyl, $C_6$-$C_{20}$ branched cyclic alkyl, $C_6$-$C_{20}$ linear alkenyl, $C_6$-$C_{20}$ branched alkenyl, $C_6$-$C_{20}$ cyclic alkenyl, $C_6$-$C_{20}$ branched cyclic alkenyl, $C_6$-$C_{20}$ substituted or unsubstituted aryl, the moieties which substitute the aryl units can be alkyl moieties, and mixtures thereof. In at least one exemplary embodiment, $R^1$ is a $C_8$ linear alkyl group. A denotes a linear or branched, saturated or unsaturated $C_1$ to $C_{20}$ divalent hydrocarbons which may be optionally substituted with a hydroxyl, carboxyl, carboxylate or a halogen. Examples of $C_1$ to $C_{20}$ divalent hydrocarbons include, $C_1$-$C_{20}$ linear alkylene, $C_4$-$C_{20}$ branched alkylene, $C_6$-$C_{20}$ cyclic alkylene, $C_6$-$C_{20}$ branched cyclic alkylene, $C_6$-$C_{20}$ linear alkenylene, $C_6$-$C_{20}$ branched alkenylene, $C_6$-$C_{20}$ cyclic alkenylene, $C_6$-$C_{20}$ branched cyclic alkenylene, $C_6$-$C_{20}$ substituted or unsubstituted arylene, generally the moieties which substitute the aryl units are alkyl moieties, and mixtures thereof. In at least one embodiment, A is a $C_{10}$ linear alkylene. X is an organic acid having the formula $R^4$—$COO^-$, wherein $R^4$ is hydrogen, hydroxyl, or $C_1$-$C_{40}$ alkyl. In an exemplary embodiment, suitable organic acids include but are not limited to, carboxylic acids, such as ($C_1$-$C_{40}$) alkanecarboxylic acids which, for example, are unsubstituted or substituted by halogen, saturated or unsaturated dicarboxylic acids, such as hydroxycarboxylic acids, such as amino acids, such as ($C_1$-$C_{40}$) alkylsulfonic acids. Additional embodiments of organic acids from which salts can be derived include, for example, acetic acid, propionic acid, phosphoric acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, glycyrrhizinic acid and salicylic acid. Exemplary organic acids that can be used in embodiments of the present invention include stearic acid, phosphonic acid, trifluoroacetic acid, cyanoacetic acid, benzoic acid, 4-cyanobenzoic acid, 2-chlorobenzoic acid, 2-nitrobenzoic acid, citric acid, fumaric acid, malonic acid, oxalic acid, maleic acid, phenoxyacetic acid, methanesulfonic acid, p-toluenesulfonic acid, benzenesulfonic acid, p-toluenesulfinic acid and the like.

Another aspect of the present invention is directed to an antimicrobial bispyridine amine composition, which is an octenidine distearate having the general formula:

(II)

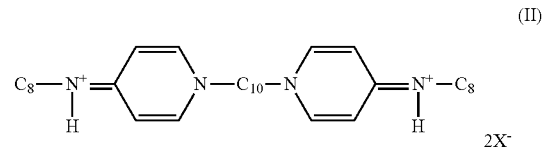

X is an anion of an organic acid having the formula $R^4$—$COO^-$, wherein $R^4$ is hydrogen, hydroxyl, or $C_1$-$C_{40}$ alkyl. Exemplary organic acids that can be used in embodiments of the present invention include, but are not limited to, carboxylic acids, such as ($C_1$-$C_{40}$) alkanecarboxylic acids which, for example, are unsubstituted or substituted by halogen, saturated or unsaturated dicarboxylic acids, such as hydroxycarboxylic acids, such as amino acids, such as ($C_1$-$C_{40}$) alkylsulfonic acids. Additional embodiments of organic acids from which salts can be derived include, for example, acetic acid, propionic acid, phosphoric acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid. Additional exemplary organic acids that can be used in embodiments of the present invention include stearic acid, phosphonic acid, trifluoroacetic acid, cyanoacetic acid, benzoic acid, 4-cyanobenzoic acid, 2-chlorobenzoic acid, 2-nitrobenzoic acid, citric acid, fumaric acid, malonic acid, oxalic acid, maleic acid, phenoxyacetic acid, methanesulfonic acid, p-toluenesulfonic acid, stearic acid, benzenesulfonic acid, p-toluenesulfinic acid and the like.

A particularly important feature of the organic salts of bispyridine amines of the present invention is their ability to remain on the surface of the skin at the location where applied while slowing bacterial growth on the skin. While not intending to be bound by any particular theory of action, this ability to remain on the surface of the skin is believed to be the result of the large molecular sizes of bispyridine amines conferred by the alkyl chain.

Preparations of deodorants come in many forms, including but not restricted to aerosol sprays, roll-ons, deodorant sticks, pumps, powders, power sprays, creams and gels. Preparations of the antimicrobial compositions of the invention can be combined with astringents such as, for example, aluminum salts such as aluminum oxychloride.

Basic aerosol deodorants typically contain alcohol, a propellant, fragrance and typically an antimicrobial agent and an emollient. Dry aerosol deodorants typically contain propellant, volatile silicone, antiperspirant salts like aluminum chlorohydrate, modified clay, and fragrance. Examples of aerosol containers that can be used in the present invention include, for example, lacquered tinplate (steel with a layer of tin), which is generally made with two or three pieces of metal crimped together, aluminum and stainless steel. Advantageously, it was discovered, as shown in Example 5, that the bispyridine amine of the present invention was less corrosive than actives, such as, for example octenidine dihydrochloride and Polyhexamethylene biguanide stearate (PHMB, polihexanide), which are commonly used in personal care and cosmetic preparations.

Deodorant solution roll-ons are typically hydroalcoholic formulations including alcohol, water, fragrance and a viscosity control agent like cellulosic gum. Deodorant emulsion roll-ons are typically oil-in-water systems containing water, oil, emulsifiers, fragrance and typically include a skin-care active and an antimicrobial agent. Stick deodorants are typically gelled glycol or hydroalcohol solutions of fragrance and deodorant active, and often contain sodium stearate or dibenzylidene sorbitol as the gellant. Antiperspirant formulations that offer both deodorant and perspiration protection are typically prepared using building blocks, such as an antiperspirant active, carrier fluids and aerosol propellants, structurants and emulsifies, sensory modifiers and fragrance. While a specific deodorant active is not usually included, such an addition could offer additional product benefits.

In a further aspect, the present invention provides the use of a compound of formula (I) or (II), or an acceptable salt thereof, in the manufacture of an antimicrobial composition for use in personal care deodorant. It is understood that the deodorant may include other components permitting a broader scope of antimicrobial and antiperspirant effect than the compounds of the present invention alone. In one embodiment, the bispyridine amine is combined with a polyalcohol. Examples of polyalcohols that can be used with the invention are provided in U.S. Publication No. US2011/0217260, which is incorporated by reference herein. Typically, the antimicrobial bispyridine amine composition according to the present invention will contain from about 0.01% to about 5%, from about 0.03% to about 3%, or from about 0.05% to about 1% by weight of the bispyridine amine of formula (I) or (II) based on the total weight of the composition in which they are present, excluding any volatile propellant.

Products of the present invention may comprise compositions taking any form. When a product comprises more than one composition, it is preferred that the compositions take the same form. Exemplary compositions of the present invention include, for example, wax-based sticks, soap-based sticks, compressed powder sticks, roll-on suspensions or solutions, emulsions, gels, creams, squeeze sprays, pump sprays, and aerosols. Each product form contains its own selection of additional components, both essential and non-essential. The types of components typical for each of the above product forms may be incorporated in the corresponding compositions of the invention.

A cosmetically acceptable carrier material is a highly desired additional component of the products of the invention. The carrier material may be hydrophobic or hydrophilic, solid or liquid. Typical carrier materials are liquids. Hydrophobic liquids suitable for use include liquid silicones, such as liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, or additionally, non-silicone hydrophobic liquids may be used. Such materials include mineral oils, hydrogenated polyisobutene, polydecene, paraffins, isoparaffins of at least 10 carbon atoms, aliphatic or aromatic ester oils (e.g. isopropyl myristate, lauryl myristate, isopropyl palmitate, diisopropyl sebecate, diisopropyl adipate, or $C_8$ to $C_{18}$ alkyl benzoates), and polyglycol ethers, for example polyglycol butanol ethers. Hydrophilic liquid carrier materials, for example water, may also be employed.

In some embodiments of the present invention, liquid carrier materials are organic solvents, such as aliphatic alcohols (monohydric or polyhydric having 2 to 8 carbon atoms) and polyglycol ethers, such as oligoglycol ethers having only 2 to 5 repeat units. Examples include dipropylene glycol, glycerol propylene glycol, butylene glycol, ethanol, propanol, isopropanol, and industrial methylated spirits. Organic solvents used in some embodiments of the present invention are aliphatic alcohols, in particular those having 2 to 3 carbon atoms, especially ethanol and isopropanol.

Mixtures of carrier materials may also be used. The total amount of carrier material employed can be at least 5%, from 30% to 99%, or from 60% to 98% by weight of the composition, excluding any volatile propellant present.

Structurants and emulsifiers are further additional components of the compositions of the invention that are highly desirable in certain product forms. Structurants, when employed, can be present at from 1% to 30% by weight of a composition, while emulsifiers can be present at from 0.1% to 10% by weight of a composition.

Suitable structurants include cellulosic thickeners such as hydroxy propyl cellulose and hydroxy ethyl cellulose, and dibenzylidene sorbitol. Other suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, and propylene carbonate. Suitable emulsifiers include steareth-2, steareth-20, steareth-21, ceteareth-20, glyceryl stearate, cetyl alcohol, cetearyl alcohol, PEG-20 stearate, dimethicone copolyol, and poloxamines.

Further emulsifiers/surfactants desirable in certain compositions of the invention are perfume solubilisers and wash-off agents. Examples of the former include PEG-hydrogenated castor oil, available from BASF in the Cremophor® RH and CO ranges, which can be present at up to 1.5% by weight, or from 0.3 to 0.7% by weight. Examples of the latter include poly(oxyethylene)ethers.

Certain sensory modifiers are further desirable components in the compositions of the invention. Such materials can be used at a level of up to 20% by weight of a composition. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely divided silica (e.g. Aerosil® 200), polyethylene (e.g. ACumist® B18), polysaccharides, corn starch, $C_{12}$-$C_{15}$ alcohol benzoate. PPG-3 myristyl ether, octyl dodecanol, $C_7$-$C_{14}$ isoparaffins, diisopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

Fragrance is also a desirable additional component in the compositions of the invention. Suitable materials include conventional perfumes, such as perfume oils and also include so-called deo-perfumes. These latter materials may also qualify as additional organic anti-microbial agents. Levels of incorporation are preferably up to 4% by weight, particularly from 0.1% to 2% by weight, and especially from 0.7% to 1.7% by weight of a composition. Synergies can exist between the essential components of the invention and certain fragrance components—long-lasting odor control being the result.

It should be noted that certain components of compositions perform more than one function. Such components are additional ingredients, their use often saving both money and formulation space. Examples of such components include ethanol, isopropyl myristate, and the many components that can act as both structurants and sensory modifiers, for example silica.

Further additional components that may also be included are colorants and preservatives.

When the present invention involves the use of an aerosol composition, a volatile propellant is an essential component of such composition. The level of incorporation of the volatile propellant is typically from 30 to 99 parts by weight and particularly from 50 to 95 parts by weight. Non-chlorinated volatile propellant can be used, in particular liquefied hydrocarbons or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. Some embodiments of the present invention employ liquefied hydrocarbon gases, and especially $C_3$ to $C_6$ hydrocarbons, including propane, isopropane, butane, isobutane, pentane, isopentane and mixtures of two or more thereof. Exemplary propellants include isobutane, isobutane/isopropane, isobutane/propane and mixtures of isopropane, isobutane, butane, and the like.

Other propellants that can be contemplated include alkyl ethers, such as dimethyl ether or compressed non-reactive gases such air, nitrogen or carbon dioxide.

Embodiments of the invention provide a safe and effective method of slowing bacterial growth on the skin. The invention also provides a safe and effective method of improving wound care products, antiperspirants and could be used in topical antimicrobial personal care products.

A more complete understanding of the present invention can be obtained by referring to the following illustrative examples of the practice of the invention, which examples are not intended, however, to limit the invention.

Example 1

Preparation of Octenidine Distearate 10 g (0.018M) of Octenidine dihydrochloride was dissolved in 200 mL of water. A solution of 7.7 g (0.092M) of $NaHCO_3$ in 40 mL of $H_2O$ was added dropwise while stirring at room temperature. The formed precipitate was filtered, dried and dissolved in 100 mL of EtOH. The resulting solution was heated to reflux followed by dropwise addition of 10.26 g (0.036M) of Stearic acid in 100 mL of EtOH preheated to 60-65° C. solution. After addition is complete the mixture is stirred at reflux for 3 h followed by solvent removal by evaporation under reduced pressure and drying of the solid residue at 60° C. under vacuum. Yield: 19.58 g of octenidine distearate.

Example 2

Analysis of Octenidine Distearate Against Skin Microorganisms In Vitro

Activities of Octenidine dihydrochloride and Octenidine distearate were tested against a range of microorganisms in a Minimum Inhibitory Concentration (MIC) test and compared against polyhexamethylene biguanide hydrochloride (PHMB). MICs for the organisms were determined using a standard 96-well microtiter plate assay in Tryptic Soy Broth (TSB) or Sabouraud Dextrose Broth (SDB).

Procedure

A stock solution (2500 ppm) of Octenidine distearate was prepared in methanol and stock solutions (2500 ppm) of Octenidine dihydrochloride and PHMB were prepared in absolute ethanol. The stock solutions were serially diluted in the 96 well plates and tested at final concentrations ranging from 625-0.31 ppm.

Bacterial inocula were grown in Tryptic Soy Broth or Brain Heart Infusion (*E. hirae*) for 24 hrs. and were adjusted to approximately one million cells per milliliter in same type of broth. Fungal inocula were grown up on Sabouraud Dextrose Agar plates (yeast) or Potato Dextrose Agar plates (mold) and mold spores and yeast cells were adjusted to approximately 100,000 per milliliter in Sabouraud Dextrose Broth (pH 5.6).

Bacterial and fungal cultures were used to inoculate the serially diluted antimicrobials in the 96 well microplate and the plate was then incubated for 48 hrs at 36° C. The lowest concentration of test compound inhibiting growth at 48 hrs. (as determined by visual inspection) was recorded as the Minimum Inhibitory Concentration (MIC)

TABLE 1

| | Microorganism | Octenidine HCl | Octenidine distearate | PHMB |
|---|---|---|---|---|
| Bacteria | *Staphylococcus aureus* (6538) | 0.61 ppm | 2.44 ppm | 1.22-2.44 ppm |
| | *Klebsiella pneumoniae* (4352) | 0.61 ppm | 2.44 ppm | 1.22-2.44 ppm |
| | *Pseudomonas aeruginosa* (9027) | 1.22 ppm | 4.88 ppm | 2.44 ppm |
| | *Pseudomonas aeruginosa* (15442) | 1.22 ppm | 19.53 ppm | 4.88 ppm |
| | *Escherichia coli* (10536) | 0.61 ppm | 2.44 ppm | 1.22 ppm |
| | *Enterococcus hirae* (8043) | 0.61 ppm | 4.88 ppm | 2.44 ppm |

TABLE 1-continued

| | Microorganism | Octenidine HCl | Octenidine distearate | PHMB |
|---|---|---|---|---|
| | *Enterobacter gergoviae* (33028) | 1.22 ppm | 4.88 ppm | 1.22-2.44 ppm |
| | *Bacillus subtilus* (6633) | 0.61 ppm | 1.22 ppm | 0.31-0.61 ppm |
| Fungi | *Aureobasidium pullulans* (9348) | 0.61 ppm | 1.22 ppm | 1.22 ppm |
| | *Gliocladium virens* (9645) | <0.31 ppm | 2.44 ppm | 0.61 ppm |
| | *Penicillium pinophilium* (11797) | <0.31 ppm | 2.44 ppm | 2.44 ppm |
| | *Paecilomyces* sp. | 78.13 ppm | 156.25 ppm | 1250-5000 ppm |
| | LB *penicillium* sp. | 0.61 ppm | 2.44 ppm | 1.22 ppm |
| | *Aspergillus niger* (16404) | 1.22 ppm | 9.77 ppm | 2.44 ppm |
| Yeast | *Candida albicans* (10231) | 0.31 ppm | 0.61 ppm | 0.61 ppm |

Example 3

Analysis of the Synergy of Octenidine Distearate and Polyhexamethylene Biguanide Stearate (PHMBS) Against Skin Microorganisms In Vitro Activities of octenidine distearate (a bispyridine amine compound of the present invention) and Polyhexamethylene biguanide stearate (PHMBS) were tested against a range of typical skin microorganisms in a Minimum Inhibitory Concentration (MIC) test. MICs for the organisms were determined using a standard 96-well microtiter plate assay in Trypic Soy Broth (TSB). A stock solution (1250 ppm) of Octenidine disterarate (Oct-S, A2768019, from Cheshire) was prepared in MeOH and a stock solution (1250 ppm) of PHMB stearate (PHMBS, Cosmocil®S, 11RC1120036 from South Plainfield) was prepared in EtOH (absolute). Bacteria were grown in Tryptic Soy Broth or Brain Heart Infusion (*E. hirae*) for 24 hrs and were adjusted to one million cells per milliliter in same type of broth. Following incubation (48 hrs at 36° C.), the lowest concentration of test compound inhibiting growth was recorded as the Minimum Inhibitory Concentration (MIC). The actives were serially diluted and tested at final concentrations ranging from 156.3-0.61 ppm. MIC was run for two different sets.

Bacteria were grown overnight in Tryptic Soy Brother (TSB) or Brain Heart Infusion (BHI) and were adjusted to approximately $1\times10^6$ colony forming units per ml (cfu/ml) and used to inoculate the wells. Final bacterial concentration in the test wells was $5\times10^5$ cfu/ml. For *Corynebacterium* spp, TSB was used for the first set and BHI for the second set. Inoculated microtiter plates were incubated at 36° C. for 48 hours.

The lowest concentration of test compound inhibiting growth was recorded as the minimum inhibitory concentration. The minimum concentration observed to completely inhibit growth was determined visually.

The synergy of octenidine distearate and PHMBS was evaluated by a two-dimensional broth micro dilution checkerboard procedure in a 96-well microplate. Similar to the MIC procedure described above, in the first column of the 96-well microplate, 0.09 ml of broth and 0.01 ml of octenidine distearate was added, and mixed with a pipetter approximately 4 times. 0.05 ml from each well of the column was then transferred to the next well of the second column and mixed as in the first column. Two-fold serial dilutions were performed for each of the remaining columns on the 96-well microplate. 0.05 ml of diluted PHMBS, from a previously diluted stock solution (7 different dilutions for each of the first seven wells of the 96-well microplate), is added to each well of the 96-well microplate, except for row H. Then, 0.1 ml of inoculum was added to each well (row H is the MIC of octenidine distearate and row L is the MIC of PHMBS). Inoculated microtiter plates were incubated at 36° C. for 48 hours. Following incubation, the lowest concentration inhibiting bacterial growth was recorded as the MIC.

For the synergy analysis, the fractional inhibitory concentration index (FICI) is calculated based on the MIC values of the individual compounds. The MIC of the serial dilutions containing both compounds was analyzed as follows:

$$FIC_A = \frac{MIC_A \text{ in combination}}{MIC_A}$$

$$FIC_B = \frac{MIC_B \text{ in combination}}{MIC_B}$$

$A$ = octenidine distearate $B = PHMBS$ $FICI = FIC_A + FIC_B$ $$\text{Mean } FICI = \frac{\text{Sum of } FICI \text{ calculated}}{\text{Number of } FICI \text{ calculated}}$$

FIC=Fractional Inhibitory Concentration

The effect of the combinations (i.e. synergic, partial synergic, indifferent or antagonist) was interpreted according to R. Bharadwaj et al, Indian J. of Pharm., 35:220-226 (2003), which is incorporated by reference herein. Synergistic action of octenidine distearate and PHMBS is present if the effect of the combination exceeds the additive effects of the individual components (synergy=mean FICI≤0.5). Partial synergy/addition is present if the additive effect of the combination of octenidine distearate and PHMBS is equal to that of the sum of the effects of the individual components (partial synergy/addition=mean FICI>0.5≤1.0). There is indifference if the effect of the combination is one that is equal to the effects of the most active component (indifference=mean FICI>1–<2.0). Antagonism between the actives is present if a reduced effect of the combination of the actives is observed in comparison with the effect of the most effective individual active (antagonism=mean FICI≥2.0).

Table 2 shows the minimum concentration of octenidine distearate and PHMBS required for an inhibitory effect against a wide range of skin bacteria. Octenidine distearate and is inhibitory to skin microflora at low concentrations making it attractive as an antimicrobial active ingredient in personal care products and cosmetics. Synergy between octenidine distearate and PHMBS was observed against *Staphylococcus epidermidis* and *Staphylococcus haemolyticus* but not against the other skin organisms.

TABLE 2

| Organism (ATCC#) | MIC (ppm)* Oct-S | PHMBS | Mean FIC | Interpretation |
|---|---|---|---|---|
| *Staphylococcus epidermidis* (12228) | 4.88-9.76 | 2.44-4.88 | 0.60 | S |
| *Staphylococcus haemolyticus* (29970) | 4.88-9.76 | 2.44-4.88 | 0.63 | S |
| *Bacillus licheniformis* (14580) | 9.76-19.53 | 2.44-4.88 | 1.29 | I |
| *Corynebacterium minutissimum* (23348) | 2.44-39.06 | 0.61-4.88 | 1.01 | I |
| *Corynebacterium xerosis* (373) | 39.06 | 9.76 | 1.38 | I |
| *Micrococcus lutetus* (4698) | >156.3-19.53 | 2.44-4.88 | 1.19 | I |

Interpretation:
S = synergy,
PS = partial synergy,
I = indifference,
A = antagonism Example 4

Comparison of the Efficacy of Octenidine Distearate to Cosmocil® S in Controlling Growth of Microorganisms on Skin To further investigate the potential of the bispyridine amine compounds of the present invention for use as antimicrobial active ingredients in personal care products and cosmetics, the efficacy of octenidine distearate in controlling growth of skin microorganisms compared to Cosmocil® S was evaluated using different skin mimics.

Testing was performed using pig skin. Although alternatives, such as VITRO-SKIN®, offered a less variable test matrix, it was decided that testing on pig skin was a better model for this application, as the pig skin allowed for actual growth of bacteria on the surface, not merely the survival of bacteria on the surface, providing more representative user skin conditions.

Preparation of Organisms

The typical skin microorganisms *Staphylococcus epidermis* (ATCC 12228), *Corynebacterium minutissimum* (ATCC 23348), *Staphylococcus haemolyticus* (ATCC 29970), *Corynebacterium xerosis* (ATCC 373), and *Micrococcus luteus* (ATCC 4698), were grown in Tryptic Soy Broth (TSB) at 35-37° C. for approximately 24 hours. Each bacterial suspension was diluted 1:50 in TSB and then inoculum was prepared by mixing equal volume of each bacterial suspension. The final inoculum was plated in TSA to get an accurate count and used as a mixed pool of bacteria.

Pig Skin Preparation

Pig skin was washed dried and cut into 1.25 inches×1.25 inches (3.175 cm×3.175 cm=10.081 $cm^2$) square samples. The skin pieces were sterilized by gamma sterilization and stored in the freezer until required. The frozen skin was thawed in the refrigerator overnight before use.

Preparation of Test Samples

Test samples of octenidine distearate, octenidine distearate in propylene glycol, and Cosmocil® S (commercial active ingredient) were each prepared in ethanol at 200 ppm.

Test Procedure

1. Solutions/suspensions were applied to triplicate samples by pipetting 100 μl over the surface and spreading with a sterile, disposable plastic inoculating loop.
2. Samples were allowed to air dry for 20 to 30 minutes.
3. A 50 μl inoculum was pipetted over the treated skin pieces and covered with a sterile microscope cover slip.
4. Except for the time zero control sample, all samples were placed under humid conditions in an incubator held at 35° C.
5. At each sampling time (0.5, 2, and 5 hours), pieces were aseptically transferred to 50 mL Modified Letheen Broth and shaken for 3 minutes before samples were plated in Tryptic Soy Agar.
6. Plates were incubated at 35-37° C. for 48 hours before the colonies were counted, and the mean values calculated.

Results and Conclusions

The experiment was performed using pig skin, which provided an environment that is closer to the normal habitat for the microorganisms. FIG. 1 shows that octenidine distearate in propylene glycol and octenidine distearate were equally as effective as Cosmocil® S over an 8 hour time period on the pig skin surface. FIG. 1 also shows that the ethanol control number drops initially at the 0.5 hour time point and then the survivors gradually build in numbers over the remainder of the test. All three active ingredients were able to control the growth of the microorganisms for 8 hours.

The skin has a lipid barrier layer and the lipophilic nature of octenidine distearate would make this material more compatible to the skin structure. Also octenidine distearate provides advantages over commonly used active agents, which allows deodorant manufacturers to package the composition in metal cans as this form would be less prone to inducing can corrosion compared to the hydrochloride form.

Because body odor is largely the result of microbial activity on the skin, a product capable of preventing the proliferation of bacteria for 8 hours is advantageous and unexpected. Moreover, it is likely that using a higher concentration of the octenidine distearate than those tested could extend the protection time.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

Example 5

Comparison of Octenidine Distearate Foaming Capabilities to PHMB

A foam height test was performed to determine if octenidine distearate possesses the same foaming capabilities inherent to PHMB.

The testing was performed on samples containing octenidine dihydrochloride, octenidine distearate, PHMB HCl and the chloride salts benzalkonium chloride, benzethonium chloride, and cetylpyridinium chloride.

A 250 ml beaker was filed with 49.5 ml of deionized (DI) water for each sample. Then, 0.5 grams of the active was added to the beaker. Each solution was blended with a Bamix® wand homogenizer/mixer for 1 minute. The solution was then poured into a 100 ml graduated cylinder with 1 ml line increments. The height of the foam was documented at an initial, 30 second, 1 minute, and 2 minute time point. Results are provided in Table 2.

TABLE 3

| Sample | Type of Foam | Initial Reading | 30 sec | 1 min | 2 min |
|---|---|---|---|---|---|
| Octenidine HCl | Slightly loose | 86 | 80 | 78 | 70 |
| Octenidine Distearate | Loose | 70 | 60 | 56 | 52 |
| PHMB HCl | Slightly loose | 87 | 85 | 80 | 75 |
| Benzalkonium Chloride | Tight | 103 | 103 | 102 | 102 |
| Benzethonium Chloride | Tight | 107 | 107 | 107 | 106 |
| Cetylpyridinium Chloride | Tight | 103 | 103 | 102 | 101 |

The results in Table 3 show that foaming capabilities of the octenidine distearate is most similar to PHMB HCl, which is thought of as a low foaming option. For use as a biocide, it is preferable to have low foaming potential. As expected, the chloride salt samples produced the most stable foams for the duration of the test.

Example 6

Corrosion Testing Comparing Octenidine and PHMB Actives

A test was performed to determine the corrosive properties of the octenidine and PHMB actives on metal samples commonly used for aerosol preparations for personal care and cosmetic products.

A 0.3% solution of each active was prepared by adding 100 grams of each active to a denatured ethanol solution. Additional solutions were prepared wherein a chelator (sodium gluconate) was added to see if the corrosion from the active could be reduced. The solutions were placed in 8 ounce glass jars with lids. A corrosion coupon made of aluminum or steel was completely submerged in each sample and was left undisturbed for 5 days (samples without chelator) or 7 days (samples with chelator). The samples were monitored daily to determine any corrosion on the coupons. On either day 5 or 7, the corrosion coupon was removed from the jar, dried, and photographed. The samples were visually examined to determine the degree and location of the corrosion. The results are provided in Table 4.

TABLE 4

| Sample | Active % in ethanol | Type of Coupon | Time | Results |
|---|---|---|---|---|
| 1 | 0.3% Octenidine HCl added directly | Aluminum | 5 days | Corrosion on majority of coupon |
| 2 | 0.3% Octenidine Stearate added directly | Aluminum | 5 days | Vey little corrosion except where precipitate formed |
| 3 | 0.3% Octenidine HCl added directly | Steel | 5 days | Corrosion mainly on edges of coupon |
| 4 | 0.3% Octenidine Stearate added directly | Steel | 5 days | Very little corrosion |
| 5 | 0.3% Octenidine HCl added as a 20% solution in propylene glycol | Aluminum | 7 days | Uniform corrosion on majority of coupon |
| 6 | 0.3% Octenidine Stearate added as a 30% solution in propylene glycol | Aluminum | 7 days | Vey little corrosion except where precipitate formed |
| 7 | 0.3% PHMB HCl added as a 20% solution in propylene glycol | Aluminum | 7 days | Corrosion on majority of coupon |
| 8 | 0.3% PHMB Stearate added as a 30% solution in propylene glycol | Aluminum | 7 days | No corrosion |
| 9 | 0.3% stearic acid added directly | Aluminum | 7 days | No corrosion |
| 10 | 0.3% octenidine stearate and 0.1% sodium gluconate (not completely solubilized) added directly) | Aluminum | 7 days | Very little corrosion except where precipitate formed, formation of precipitate took longer to form compared to samples 2 and 4 and less precipitate was present in the solution. |

Figure 2:
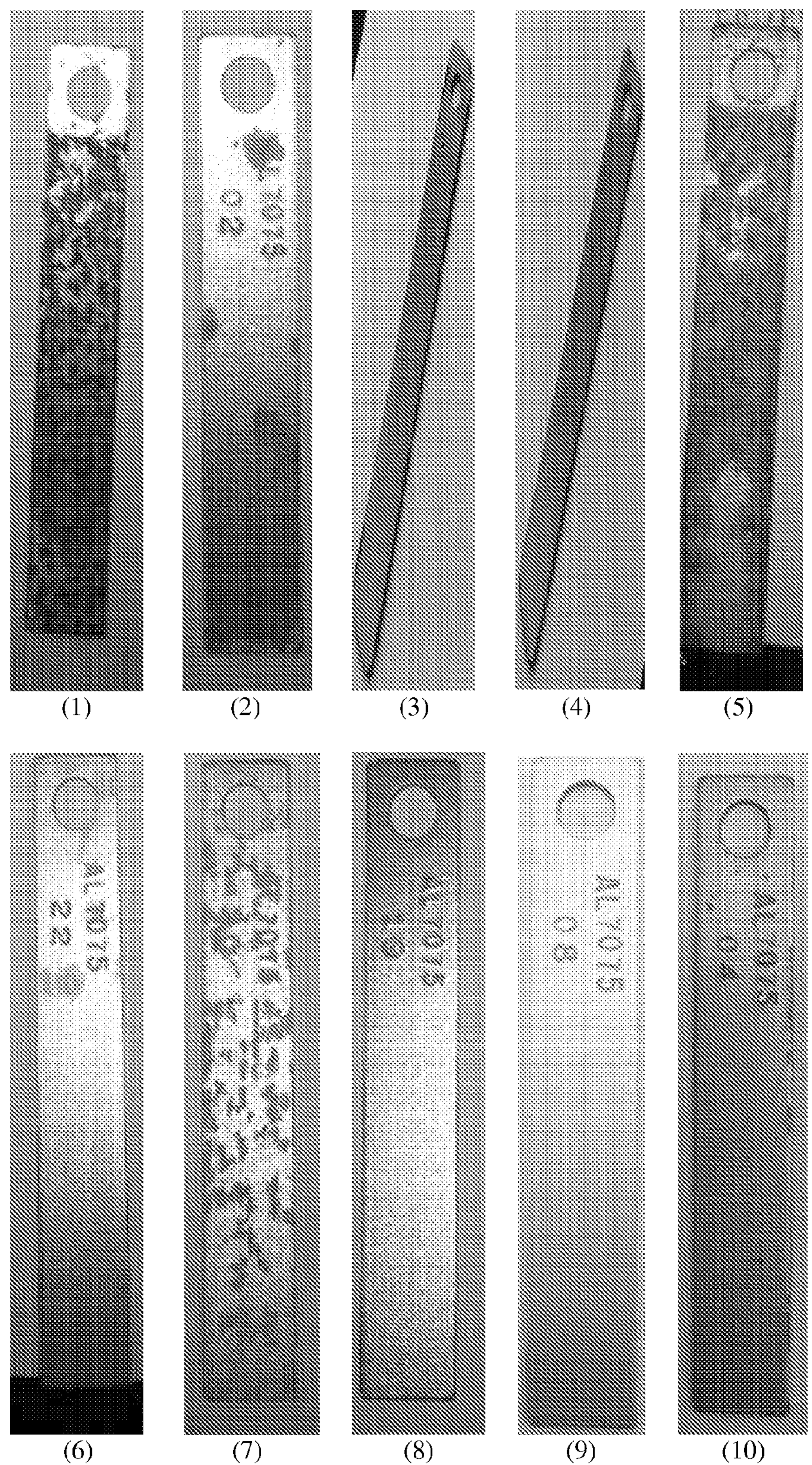
FIG. 2 depicts the corrosion on (1) an aluminum coupon following exposure to 0.3% octenidine dihydrochloride, (2) an aluminum coupon following exposure to 0.3% octenidine distearate, (3) a steel coupon following exposure to 0.3% octenidine dihydrochloride, (4) a steel coupon following exposure to 0.3% octenidine distearate, (5) an aluminum coupon following exposure to 0.3% octenidine dihydrochloride added as a 20% solution in propylene glycol, (6) an aluminum coupon following exposure to 0.3% octenidine distearate added as a 30% solution in propylene glycol, (7) an aluminum coupon in 0.3% polyhexamethylene biguanide hydrochloride (PHMB) added as a 20% solution in propylene glycol, (8) an aluminum coupon following exposure to 0.3% PHMBS added as a 20% solution in propylene glycol, (9) an aluminum coupon following exposure to 0.3% stearic acid, and (10) an aluminum coupon following exposure to 0.3% octenidine distearate and 0.1% sodium gluconate.

As shown in FIG. 2, the corrosion coupons made of aluminum or steel, which were submerged in samples containing octenidine distearate active (i.e., samples 2, 4, 6 and 10), showed very little corrosion. The corrosion coupons submerged in samples containing octenidine dihydrochloride (i.e., samples 1, 3 and 5) showed a much greater degree of corrosion when compared to the octenidine distearate active samples. Sample 7 (PHMB HCl) has significant corrosion but is much less than the octenidine dihydrochloride sample, in comparison the PHMBS (sample 8) showed no corrosion. Consequently, due to the unexpected benefit of being less corrosive than octenidine dihydrochloride, octenidine distearate would be valuable for use as an active ingredient in personal care and cosmetic applications where a metal aerosol container is used.

Example 7

Comparison of the Dermal Irritation and Toxicity Potential of Octenidine Distearate and Octenidine Dihydrochloride The MatTek EpiDerm™ MTT Viability Assay (MatTek Corp.) was utilized to determine the dermal irritancy and toxicology of octenidine distearate and octenidine dihydrochloride. The assay was performed using the EpiDerm™ Skin Model (EPI-200) as well as the Methyl thiazole tetrazolium (MT) Kit (MTT-100). The EpiDerm™ Skin Model closely parallels human skin, thus providing a useful in vitro method to assess dermal irritancy and toxicology.

MatTek EpiDerm™ tissue samples were treated in duplicate with the test articles (as a 1.25% w/v dilution in water) and positive controls for the various exposure times provided below. Negative controls (treated with tissue culture water) were tested at 4 hours only. Following treatment, the viability of the tissues was determined using MTT uptake and reduction. The absorbance of each sample was measured at 540 nm using a reference wavelength of 690 nm. The viability was then expressed as a percent of Negative Control or Vehicle Control values. The mean percent viability for each time point was used to calculate and $ET_{50}$, which represents the time at which the EpiDerm™ tissue viability was reduced 50%, compared to Negative Control or Vehicle Control tissues. The $ET_{50}$ scores were converted to an irritancy classification.

Sample Preparation

NAB Plankton Extract—25%

MTT Reduction: 25 μl of the test article were added to 75 μl of tissue culture water ($TCH_20$) to yield a 25% v/v solution. 150 μl of the test article were added to 450 μl of $TCH_20$ to yield a 25% v/v solution. 75 μl of the test article were added to 225 μl of $TCH_20$ to yield a 25% solution (clear colorless liquid).

Octenidine Distearate—1.25%

MTT Reduction: 704 μl of mineral oil were heated at 70 C for 10 minutes. 8.8 mg of the test article were added and the mixture was heated for an additional 10 minutes, with vortexing, to yield a homogeneous suspension (cloudy white liquid). 7.2 mg of the test article were crushed, added to 576 μl of warm (at 70° C. for 10 minutes) mineral oil, and vortexed (cloudy white liquid). 7.0 mg of the test article were crushed, added to 560 μl of warm (at 70° C. for 10 minutes) mineral oil, and vortexed (cloudy white liquid).

Octenidine Dihydrochloride—1.25%

12.5 mg of the test article were brought to a volume of 1 ml with tissue culture water, warmed to 50° C. in a water bath until the test article went into solution, and mixed to yield a 1.25% dilution (clear colorless liquid).

Procedures

EpiDerm™ Tissue Samples

EpiDerm™ tissues, Lots 16454 Kits K and R and 17402 Kit A, were received from MatTek and refrigerated at 2-8° C. Before use, tissues were incubated (37° C.±1 C, 5%±1% $CO_2$) with assay medium (MatTek) for a one-hour equilibration. Equilibration medium was replaced with fresh medium before dosing.

Test Article Reduction of MTT

The test articles were diluted as described in the sample preparation above. 100 μl of the test article dilution were mixed with 1 ml of MTT solution (1 mg/ml MTT diluted in Dulbecco's Modified Eagle's Medium (DMEM). A negative control (100 μl of tissue culture water) and a vehicle control (100 μl of mineral oil) were tested concurrently. The solutions were incubated at room temperature in the dark for 60 minutes. After incubation, the solutions were visually inspected for purple coloration, which is a positive indication that the test article reduced MTT. Since tissue viability is based on MTT reduction, direct reduction by a test article can exaggerate viability, making a test article seem less irritating that it really is. Neither of the test articles nor the vehicle control were found to have reduced MTT and the assay continued as per the protocol.

Dosing

Test article NAB plankton extract—25%, was dosed diluted to 25% in tissue culture water ($TCH_20$), octenidine distearate—1.25% was dose diluted to 1.25% in mineral oil and octenidine dihydrochloride—1.25%, was dose diluted to 1.25% in tissue culture water ($TCH_20$). 100 μl of the test article dilutions were applied to the top of each EpiDerm™ tissue. The test articles remained in contact with the EpiDerm™ tissue for 1, 4 and 24 hours. Vehicle controls ($TCH_20$ and mineral oil) for the test articles were tested at 4 hours. A positive control (1% Triton® X-100) was tested at 4 and 9 hours. A negative control ($TCH_20$) was tested at 4 hours. Each treatment with test article or control was conducted in duplicate.

Tissue Viability (MTT Reduction)

At the end of the selected exposure periods, each EpiDerm™ tissue was rinsed with phosphate buffered saline (PBS) and transferred to a 24-well plate containing 300 μl of MTT solution (1 mg/ml MTT in DMEM). The tissues were then returned to the incubator for three-hour MTT incubation period. Following the MTT incubation period, each EpiDerm™ tissue was rinsed and then treated overnight with 2.0 ml of extractant solution (isopropanol) per well. An aliquot of the extracted MTT formazan was measured at 540 nm using a plate reader (pQuant Plate Reader, Bio-Tek Instruments, Winooski, Vt.), subtracting the absorbance at a reference wavelength of 690 nm.

Analysis of Data:

The mean absorbance value for each time point was calculated from the optical density (OD) of the duplicate samples and expressed as percent viability for each sample using the following formula:

% viability=100×(OD sample/OD negative control or vehicle control)

The $ET_{50}$, the time at which the EpiDerm™ tissue viability was reduced 50% compared to control tissues, was then determined using a macro in Microsoft Excel 5.0, provided by MatTek, using the equation:

$$V=a+b \log t$$

Where V=percent viability, t=time in hours, and a and b are constants that can be determined by using the viability data for two different exposure times of the text article to the tissue. These exposure times must yield viabilities that flank 50%.

Correlation of in vitro and in vivo results are provided in Table 5 in order to assign expected in vivo irritancy responses based on the ET50 results obtained using the EpiDerm MTT viability assay.

TABLE 5

| Expected In vivo irritancy | Example | ET50 (hrs.) |
|---|---|---|
| Severe, Probably Corrosive | Concentrated Nitric acid | <0.5 |
| Moderate | 1% Sodium Dodecyl Sulfate | 0.5-4 |
| Moderate to Mild | 1% Triton X-100 | 4-12 |
| Very Mild | Baby shampoo | 12-24 |
| Non-irritating | 10% Tween ® 20 | >24 |

Results

Results for octenidine distearate and octenidine dihydrochloride using the MatTek EpiDerm™ MTT viability assay are provide below in Table 6. The $ET_{50}$ of the positive control (1.0% Triton® X-100) was 5.8 and 5.9 for the testing of octenidine distearate and octenidine dihydrochloride, respectively, which fall within MatTek's acceptance range of 4.8-8.7 hours. The $ET_{50}$ of octenidine dihydrochloride was 1.1, which indicates a moderate irritant. The $ET_{50}$ of octenidine distearate was greater than 24.0, which indicates that it is not a dermal irritant. Consequently, in surprising contrast to octenidine dihydrochloride, octenidine distearate does not show potential skin hazards, which makes is more favorable for topical application.

TABLE 6

| SAMPLE | Exposure Times | $ET_{50}$ (hrs) | Irritancy Classification |
|---|---|---|---|
| NAB Plankton Extract - 25% | 1, 4, 24 | >24.0 | Non-Irritating |
| Octenidine Distearate - 1.25% | 1, 4, 24 | >24.0 | Non-Irritating |
| Octenidine dihydrochloride - 1.25% | 1, 4, 24 | 1.1 | Moderate |
| 1.0% Triton ® X-100 (positive control) | 4, 9 | 5.8, 5.9 | Within Range (4.8-8.7) |

Example 8

Comparison of the Ocular Irritation and Toxicity Potential of Octenidine Distearate and Octenidine Dihydrochloride The MatTek EpiOcular™ MTT Viability Assay (MatTek Corp.) was utilized to assess ocular irritancy and toxicology of octenidine distearate and octenidine dihydrochloride. The assay was performed using the MatTek EpiOcular™ Tissue Model (OCL-200) as well as the Methyl thiazole tetrazolium (MT) Kit (MT-100). The EpiOcular™ Tissue Model closely parallels human ocular tissue, thus providing a useful in vitro method to assess ocular irritancy and toxicology.

Sample Preparation

NAB Plankton Extract—25%

MTT Reduction: 25 µl of the test article were added to 75 µl of tissue culture water ($TCH_20$) to yield a 25% v/v solution. 100 µl of the test article were added to 300 µl of $TCH_20$ and vortexed to yield a 25% v/v solution (clear colorless liquid). 200 µl of the test article were added to 600 µl of $TCH_20$ to yield a 25% solution (clear colorless liquid).

Octenidine Distearate—1.25%

MTT Reduction: 704 µl of mineral oil were heated at 70° C. for 10 minutes. 8.8 mg of the test article were added and the mixture was heated for an additional 10 minutes, with vortexing, to yield a homogeneous suspension (cloudy white liquid). 7.4 mg of the test article were crushed, added to 592 µl of warm (70° C. for 10 minutes) mineral oil, and vortexed (cloudy white liquid). 9.4 mg of the test article were crushed, added to 752 µl of warm (70° C. for 10 minutes) mineral oil, and vortexed (cloudy white liquid).

Octenidine Dihydrochloride—1.25%

12.5 mg of the test article were brought to a volume of 1 ml with tissue culture water, warmed to 50° C. in a water bath until the test article went into solution, and mixed to yield a 1.25% dilution (clear colorless liquid).

Controls 0.3% Triton® X-100 (MatTek) (clear liquid) was used as a positive control. Tissue culture water ($TCH_20$) (Sigma) (clear liquid) was used as a negative control. Mineral oil (Sigma) (clear liquid) was used as a vehicle control.

Procedures

EpiOcular™ Tissue Samples

EpiOcular™ tissues, Lots 15075 Kits A and B were received from MatTek and refrigerated at 2-8° C. Before use, tissues were incubated (37° C.±1° C., 5%±1% $CO_2$) with assay medium (MatTek) for a one-hour equilibration. Equilibration medium was replaced with fresh medium before dosing.

Test Article Reduction of MTT

The test articles were diluted as described in the sample preparation above. 100 µl of the test article dilution were mixed with 1 ml of MTT solution (1 mg/ml MTT diluted in Dulbecco's Modified Eagle's Medium (DMEM). A negative control (100 µl of tissue culture water) and a vehicle control (100 µl of mineral oil) were tested concurrently. The solutions were incubated at room temperature in the dark for 60 minutes. After incubation, the solutions were visually inspected for purple coloration, which is a positive indication that the test article reduced MTT. Since tissue viability is based on MTT reduction, direct reduction by a test article can exaggerate viability, making a test article seem less irritating that it really is. Neither of the test articles nor the vehicle control were found to have reduced MTT and the assay continued as per the protocol.

Dosing

Test article NAB plankton extract—25%, was dosed diluted to 25% in tissue culture water ($TCH_20$), octenidine distearate—1.25% was dose diluted to 1.25% in mineral oil and octenidine dihydrochloride—1.25%, was dose diluted to 1.25% in tissue culture water ($TCH_20$). 100 µl of the test article dilutions were applied to the top of each EpiOcular™ tissue. Initially, duplicate EpiOcular™ tissues were exposed to the test article for 16 minutes. The MTT viability at the 16-minute time point for each test article was greater than 90%, so additional tissues were treated for 64 and 256 minutes. A negative control was tested using tissue culture water at 16 minutes. A vehicle control (mineral oil) was tested for 16 minutes. A positive control (0.3% Triton® X-100) was tested at 15 and 45 minutes. Each treatment with test article or control was conducted in duplicate.

Tissue Viability (MTT Reduction)

At the end of the selected exposure periods, each EpiOcular™ tissue was rinsed with phosphate buffered saline (PBS), soaked for 10 minutes in assay medial and transferred to a 24-well plate containing 300 µl of MTT solution (1 mg/ml MTT in DMEM). The tissues were then returned to the incubator for three-hour MTT incubation period. Following the MTT incubation period, each EpiOcular™ tissue was rinsed with PBS and then treated overnight with 2.0 ml of extractant solution (isopropanol) per well. An aliquot of the extracted MTT formazan was measured at 540 nm using a plate reader (µQuant Plate Reader, Bio-Tek Instruments, Winooski, Vt.), subtracting the absorbance at a reference wavelength of 690 nm.

Analysis of Data:

The mean absorbance value for each time point was calculated from the optical density (OD) of the duplicate samples and expressed as percent viability for each sample using the following formula:

$$\%\ \text{viability}=100\times(\text{OD sample}/\text{OD negative control or vehicle control})$$

The $ET_{50}$, the time at which the EpiOcular™ tissue viability was reduced 50% compared to control tissues, was then determined using a macro in Microsoft Excel 5.0, provided by MatTek, using the equation:

$$V=a+b\log t$$

Where V=percent viability, t=time in hours, and a and b are constants that can be determined by using the viability data for two different exposure times of the text article to the tissue. These exposure times must yield viabilities that flank 50%.

Correlation of in vitro and in vivo results are provided in Table 7 in order to assign expected in vivo irritancy responses based on the $ET_{50}$ results obtained using the EpiOcular™ MTT viability assay.

TABLE 7

| | | EpiOcular ™ $ET_{50}$ (min) | |
|---|---|---|---|
| Irritancy Classification | Example | Standard Method* | Specific Gravity Method** |
| Non-irritating, Minimal | PEG-75 Lanolin, Tween ® 20 | >60 | >256-26.5 |
| Mild | 3% Sodium dodecyl sulfate (SDS) | 30-60 | <26.5-11.7 |
| Moderate | 5% Triton ® X-100 | 3-29.99 | <11.7-3.45 |
| Severe, Extreme | %5 Benzalkonium Chloride | <3 | <3.45 |

*= ET50 ranges as defined by the MatTek protocol "Neat Method for Ocular Irritation"
**= ET50 ranges as defined by the MatTek protocol "Dilution Method for Ocular Irritation"

Result

Results for octenidine distearate and octenidine dihydrochloride using the MatTek EpiOcular™ MTT viability assay are provide below in Table 8. The $ET_{50}$ of the positive control (0.3% Triton® X-100) was 24.8 and 28.1 for the testing of octenidine distearate and octenidine dihydrochloride, respectively, which fall within the assays acceptance range of 12.2-37.5 hours. The $ET_{50}$ of octenidine dihydrochloride was <1.1, which indicates a severe irritant. The $ET_{50}$ of octenidine distearate was greater than 256.0, which indicates that it is a non-irritant or causes minimal irritation. Consequently, in surprising contrast to octenidine dihydrochloride, octenidine distearate does not show potential ocular irritancy or toxicity, which makes is more favorable for topical ocular applications.

TABLE 8

| SAMPLE | $ET_{50}$ (min) | Irritancy Classification |
|---|---|---|
| NAB Plankton Extract - 25% | >256.0 | Non-Irritating, minimal |
| Octenidine Distearate - 1.25% | >256.0 | Non-Irritating, minimal |
| Octenidine dihydrochloride - 1.25% | <1.1 | Severe |
| 0.3% Triton ® X-100 (positive control) | 24.8, 28.1 | Within Range (12.2-37.5) |

What is claimed is:

1. A topical antimicrobial composition comprising a bispyridine amine salt of formula (I):

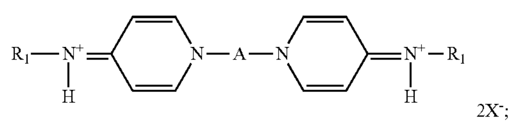

wherein $R^1$ is selected from a group consisting of hydrogen, $C_1$-$C_{20}$ linear alkyl, $C_4$-$C_{20}$ branched alkyl, $C_6$-$C_{20}$ cyclic alkyl, $C_6$-$C_{20}$ branched cyclic alkyl, $C_6$-$C_{20}$ linear alkenyl, $C_6$-$C_{20}$ branched alkenyl, $C_6$-$C_{20}$ cyclic alkenyl, $C_6$-$C_{20}$ branched cyclic alkenyl, $C_6$-$C_{20}$ aryl, and $C_6$-$C_{20}$ substituted aryl;

A is selected from a group consisting of $C_1$-$C_{20}$ linear alkylene, $C_4$-$C_{20}$ branched alkylene, $C_6$-$C_{20}$ cyclic alkylene, $C_6$-$C_{20}$ branched cyclic alkylene, $C_6$-$C_{20}$ linear alkenylene, $C_6$-$C_{20}$ branched alkenylene, $C_6$-$C_{20}$ cyclic alkenylene, $C_6$-$C_{20}$ branched cyclic alkenylene, $C_6$-$C_{20}$ arylene, and $C_6$-$C_{20}$ substituted arylene; and X is an organic acid having the formula $R^4$—$COO^-$, wherein $R^4$ is hydrogen, hydroxyl, or $C_1$-$C_{40}$ alkyl;

and wherein said topical antimicrobial composition is a deodorant or antiperspirant composition.

2. The topical antimicrobial composition of claim 1 wherein $R^1$ is a $C_8$ linear alkyl group and A is a $C_{10}$ linear alkylene.

3. A method for providing an antimicrobial effect to a skin, said method comprising applying to the skin a pharmaceutically effective amount of a topical antimicrobial composition, said topical antimicrobial composition comprising a bispyridine amine salt of formula (I):

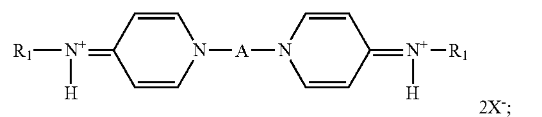

wherein $R^1$ is selected from a group consisting of hydrogen, $C_1$-$C_{20}$ linear alkyl, $C_4$-$C_{20}$ branched alkyl, $C_6$-$C_{20}$ cyclic alkyl, $C_6$-$C_{20}$ branched cyclic alkyl, $C_6$-$C_{20}$ linear alkenyl, $C_6$-$C_{20}$ branched alkenyl, $C_6$-$C_{20}$ cyclic alkenyl, $C_6$-$C_{20}$ branched cyclic alkenyl, $C_6$-$C_{20}$ aryl, and $C_6$-$C_{20}$ substituted aryl;

A is selected from a group consisting of $C_1$-$C_{20}$ linear alkylene, $C_4$-$C_{20}$ branched alkylene, $C_6$-$C_{20}$ cyclic alkylene, $C_6$-$C_{20}$ branched cyclic alkylene, $C_6$-$C_{20}$ linear alkenylene, $C_6$-$C_{20}$ branched alkenylene, $C_6$-$C_{20}$ cyclic alkenylene, $C_6$-$C_{20}$ branched cyclic alkenylene, $C_6$-$C_{20}$ arylene, and $C_6$-$C_{20}$ substituted arylene; and X is an organic acid having the formula $R^4$—$COO^-$, wherein $R^4$ is hydrogen, hydroxyl, or $C_1$-$C_{40}$ alkyl.

4. A method for reducing or eliminating malodor which comprises administering to the skin an effective amount of a topical antimicrobial composition, said topical antimicrobial composition comprising a bispyridine amine salt of formula (I):

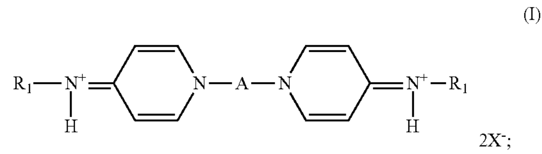

wherein $R^1$ is selected from a group consisting of hydrogen, $C_1$-$C_{20}$ linear alkyl, $C_4$-$C_{20}$ branched alkyl, $C_6$-$C_{20}$ cyclic alkyl, $C_6$-$C_{20}$ branched cyclic alkyl, $C_6$-$C_{20}$ linear alkenyl, $C_6$-$C_{20}$ branched alkenyl, $C_6$-$C_{20}$ cyclic alkenyl, $C_6$-$C_{20}$ branched cyclic alkenyl, $C_6$-$C_{20}$ aryl, and $C_6$-$C_{20}$ substituted aryl;

A is selected from a group consisting of $C_1$-$C_{20}$ linear alkylene, $C_4$-$C_{20}$ branched alkylene, $C_6$-$C_{20}$ cyclic alkylene, $C_6$-$C_{20}$ branched cyclic alkylene, $C_6$-$C_{20}$ linear alkenylene, $C_6$-$C_{20}$ branched alkenylene, $C_6$-$C_{20}$ cyclic alkenylene, $C_6$-$C_{20}$ branched cyclic alkenylene, $C_6$-$C_{20}$ arylene, and $C_6$-$C_{20}$ substituted arylene; and X is an organic acid having the formula $R^4$—$COO^-$, wherein $R^4$ is hydrogen, hydroxyl, or $C_1$-$C_{40}$ alkyl.

5. The topical antimicrobial composition of claim 1 wherein the composition is a deodorant composition.

6. The topical antimicrobial composition of claim 1 wherein the composition is an antiperspirant composition.

7. The method for providing an antimicrobial effect of claim 3 wherein the composition is administered from an airborne, liquid, or solid vehicle.

8. The topical antimicrobial composition of claim 1, wherein the bispyridine amine salt has the formula (II):

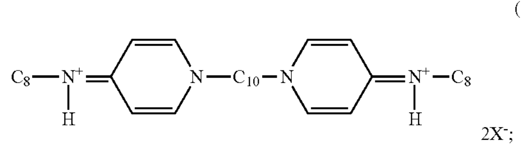

wherein X is an organic acid having the formula $R^4$—$COO^-$, wherein $R^4$ is hydrogen, hydroxyl, or $C_1$-$C_{40}$ alkyl.

9. The method for providing an antimicrobial effect of claim 3, wherein the bispyridine amine salt has the formula (II):

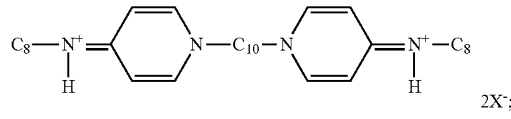

wherein X is an organic acid having the formula $R^4$—$COO^-$, wherein $R^4$ is hydrogen, hydroxyl, or $C_1$-$C_{40}$ alkyl.

10. The topical antimicrobial composition of claim 8 wherein the composition is a deodorant composition.

11. The topical antimicrobial composition of claim 8 wherein the composition is an antiperspirant composition.

12. The method for providing an antimicrobial effect of claim 9 wherein the composition is administered from an airborne, liquid, or solid vehicle.

13. The topical antimicrobial composition of claim 10 wherein the deodorant composition is an antiperspirant.

14. The method for reducing or eliminating malodor of claim 4 wherein the composition is administered from an airborne, liquid, or solid vehicle.

15. The method for reducing or eliminating malodor of claim 4, wherein the bispyridine amine salt has the formula (II):

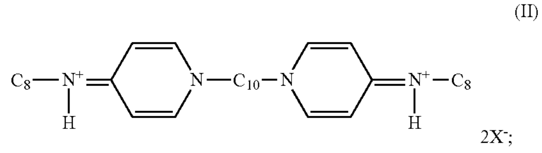

wherein X is an organic acid having the formula $R^4$—$COO^-$, wherein $R^4$ is hydrogen, hydroxyl, or $C_1$-$C_{40}$ alkyl.

16. The method for reducing or eliminating malodor of claim 15 wherein the composition is administered from an airborne, liquid, or solid vehicle.

17. The topical antimicrobial composition of claim 8, wherein X is a stearate.

* * * * *